(12) United States Patent
Baird et al.

(10) Patent No.: US 10,513,946 B2
(45) Date of Patent: Dec. 24, 2019

(54) CONDENSATION IRRADIATION SYSTEM

(71) Applicant: ROLLS-ROYCE PLC, London (GB)

(72) Inventors: Matthew Baird, Derby (GB); Adriano Pulisciano, Birmingham (GB); Graham Watson, Derby (GB)

(73) Assignee: ROLLS-ROYCE plc, London (GB)

( * ) Notice: Subject to any disclaimer, the term of this patent is extended or adjusted under 35 U.S.C. 154(b) by 275 days.

(21) Appl. No.: 15/592,586

(22) Filed: May 11, 2017

(65) Prior Publication Data
US 2017/0350272 A1 Dec. 7, 2017

(30) Foreign Application Priority Data
Jun. 6, 2016 (GB) .................. 1609820.4

(51) Int. Cl.
| | | |
|---|---|---|
| F01D 21/00 | (2006.01) | |
| F04D 27/00 | (2006.01) | |
| G01N 21/85 | (2006.01) | |
| F02K 3/06 | (2006.01) | |
| G01N 21/53 | (2006.01) | |
| F01D 21/14 | (2006.01) | |
| F02C 7/04 | (2006.01) | |
| G01N 21/47 | (2006.01) | |
| G01N 21/84 | (2006.01) | |

(52) U.S. Cl.
CPC .......... *F01D 21/003* (2013.01); *F01D 21/14* (2013.01); *F02C 7/04* (2013.01); *F02K 3/06* (2013.01); *F04D 27/001* (2013.01); *G01N 21/53* (2013.01); *G01N 21/85* (2013.01); *F05D 2220/323* (2013.01); *F05D 2220/36* (2013.01); *F05D 2260/12* (2013.01); *F05D 2270/311* (2013.01); *G01N 2021/4702* (2013.01); *G01N 2021/8405* (2013.01); *G01N 2021/8578* (2013.01)

(58) Field of Classification Search
CPC ..................................................... F01D 21/003
USPC ........................................................ 356/337
See application file for complete search history.

(56) References Cited

U.S. PATENT DOCUMENTS

| | | | |
|---|---|---|---|
| 7,933,002 B2 * | 4/2011 | Halldorsson .............. | G01P 5/26 356/28 |
| 2007/0147467 A1 * | 6/2007 | Arnold .................. | G01N 25/68 374/28 |

(Continued)

FOREIGN PATENT DOCUMENTS

| | | |
|---|---|---|
| DE | 4135930 C1 | 11/1992 |
| EP | 2570631 A2 | 3/2013 |

(Continued)

OTHER PUBLICATIONS

Dec. 7, 2016 Search Report issued in British Patent Application No. 1609820.4.

(Continued)

*Primary Examiner* — Tarifur R Chowdhury
*Assistant Examiner* — Omar H Nixon
(74) *Attorney, Agent, or Firm* — Oliff PLC

(57) ABSTRACT

A condensation irradiation system is disclosed comprising an electromagnetic radiation emitter mounted on a locating structure, the locating structure being arranged in use to position the radiation emitter so as radiation emitted therefrom travels through a condensation detection region adjacent an upstream side of a gas turbine engine fan.

15 Claims, 2 Drawing Sheets

(56) References Cited

U.S. PATENT DOCUMENTS

Figure 1:
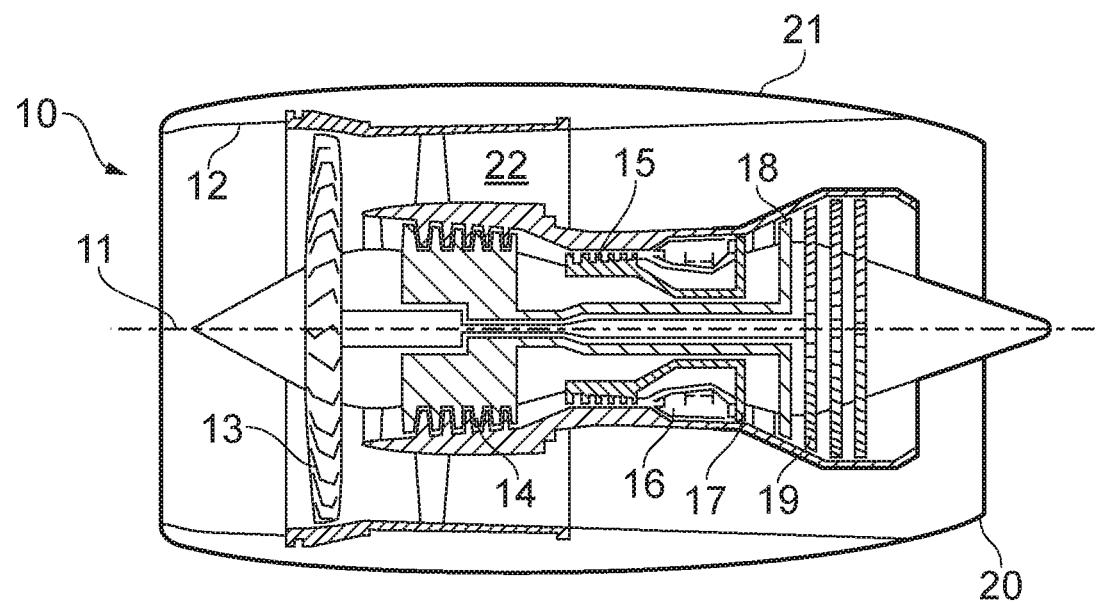

| | | | | |
|---|---|---|---|---|
| 2009/0271941 | A1* | 11/2009 | Coburn | A47L 5/32 15/334 |
| 2011/0019193 | A1* | 1/2011 | Danno | G01J 3/4338 356/433 |
| 2012/0219398 | A1* | 8/2012 | Sheard | F04D 19/002 415/1 |
| 2013/0055697 | A1* | 3/2013 | Deguchi | G01N 21/65 60/39.24 |
| 2013/0247540 | A1* | 9/2013 | Kell | F02C 7/00 60/39.091 |
| 2014/0026562 | A1* | 1/2014 | Brueck | F02C 7/00 60/605.1 |
| 2014/0277791 | A1* | 9/2014 | Lenard | B60K 6/20 700/287 |
| 2015/0330310 | A1* | 11/2015 | deGaribody | G01S 17/58 701/100 |

FOREIGN PATENT DOCUMENTS

| | | |
|---|---|---|
| JP | 2004-257876 A | 9/2004 |
| WO | 2005/033675 A1 | 4/2005 |

OTHER PUBLICATIONS

Oct. 20, 2017 Search Report issued in European Patent Application No. 17170559.

Potter, Jason et al. "Optical Condensation Measurement in Gas Turbine Engine Inlets;" Proceedings Optical Diagnostics of Living Cells II; Nov. 21, 1997; vol. 3172; pp. 424-435.

Blake, J.C.; "Effects of Condensation in JT9D Turbofan Engine Bellmouth Inlet;" AIAA/SAE 11th Propulsion Conference; Sep. 29, 1975; pp. 1-9.

\* cited by examiner

CONDENSATION IRRADIATION SYSTEM

The present disclosure concerns a condensation irradiation system and a method of detecting condensation. The system may have particular application to detection of condensation associated with a fan of an aero gas turbine engine on test or during overhaul. This is not however intended to be limiting and the disclosure may, for example, have further application to detection of condensation associated with a fan of marine or industrial power generation gas turbine engines during test or overhaul. In service applications are also envisaged for any of these gas turbine engine types.

Condensation may be prone to forming within the inlet of gas turbine engines (particularly adjacent the fan on its upstream side) due to the large pressure drop present. The pressure drop reduces the temperature of the air and, depending on the humidity, particulate count and other factors, condensation may form.

Condensation forming within the inlet of gas turbines may cause difficulties, particularly during development and pass-off testing. In particular it may cause errors in the instrumentation readings and increased fan work. By way of example this can give rise to inaccurate temperature readings during development testing and errors in engine trim setting during pass-off testing.

In order to address such difficulties the presence of condensation is currently inferred via observation of temperature variations in the airstream measured by rakes located behind the fan of heavily instrumented test engines. The use of rake data has led to the introduction of humidity limits governing the conditions under which development engines can be run. The down time dictated by these limits represents a significant cost. Furthermore it is known that the humidity limits are likely to be conservative. Condensation forms around the annulus of an intake of the engine as it moves from low to high power. This formation is erratic and can occur at any radial location within the inlet. Rakes, being positioned at particular discrete locations downstream of the fan, and in any case not detecting condensation directly, can only provide limited information on condensation formation. Further due to the small number of heavily instrumented development engines that are operated, it is only possible to gather a limited number of data points to investigate condensation formation. It is also noteworthy that rakes are not suitable for fitment to in service engines and so are not suitable for gathering in service condensation information.

The use of solid state condensation or dew point sensors that detect condensation forming on their surface has been considered. As previously mentioned however the formation of condensation is erratic and can occur at any radial location within an intake. Such sensors are therefore incapable of detecting condensation as it forms in alternative locations.

According to a first aspect there is provided a condensation irradiation system comprising an electromagnetic radiation emitter mounted on a locating structure, the locating structure being arranged in use to position the radiation emitter so as radiation emitted therefrom travels through a condensation detection region adjacent an upstream side of a gas turbine engine fan. The emitted radiation may tend to scatter where it is incident on any condensation water droplets present in the detection region. This scattered radiation may be detectable (e.g. using a camera) and may improve the contrast provided by condensation from a detection perspective. The electromagnetic radiation may therefore be considered to illuminate any condensation. With improved contrast provided by the radiation it may be possible to more accurately determine whether condensation is present and even to map the location and optionally evolution of condensation within the detection region.

Since detection may be enhanced in any location where electromagnetic radiation is present, greater or complete coverage of the area adjacent the upstream side of the fan may be achieved. Specifically it may be that detection is possible at any radial and circumferential position forward of an axial projection of the fan and adjacent the fan. This potential capability may be contrasted with that provided by the provision of condensation sensors placed at discrete locations.

Condensation detection facilitated by the system may be used during development and/or pass-off and/or servicing tests. The results may allow for determination of tighter ambient humidity tolerances under which testing may be performed without condensation occurring. This may increase the number of occasions on which tests can be conducted. Condensation detection facilitated by the system may additionally or alternatively allow for improved calibration of pass-off tests to allow for condensation induced uncertainty.

There may further be in service applications, especially where increased weight penalties are less severe (e.g. marine and industrial power generation gas turbines) or where components of the system have additional functions. Condensation detection and/or mapping facilitated by the system may provide opportunities to more accurately trim in service engines (e.g. to avoid over thrust that might otherwise reduce service intervals and/or increase servicing cost).

In some embodiments the detection region is a plane, or space bounded by planes, the plane or planes being substantially parallel with the fan plane. The emitted electromagnetic radiation may pass through the detection region travelling in a direction substantially parallel to the plane of the fan. That is the radiation may be directed across a forward face of the fan, maintaining a substantially constant distance from it at least unless it is scattered.

In some embodiments the camera is provided on the locating structure. The locating structure may position and/or orientate the camera with respect to the detection region.

In some embodiments the system comprises the fan.

In some embodiments the detection region is downstream of a spinner tip plane that is substantially parallel with the fan plane and passes through a tip of a nose cone of the fan. This region immediately adjacent the fan may be of primary consequence in terms of the presence or otherwise of condensation.

In some embodiments the locating structure comprises an intake duct arranged in use to surround the fan.

In some embodiments the system further comprises a camera oriented so as at least part of the detection region is within its field of view. The camera may be arranged to film at least part of the detection region and may therefore receive radiation emitted by the electromagnetic radiation emitter and backscattered on condensation within the detection region. The detection region should be considered to be within the field of view of the camera where the camera receives the view indirectly (e.g. a reflected view).

In some embodiments the camera is positioned so as in use the detection region is substantially between the camera and the fan. Additionally the camera may be positioned outside of an axial projection of the fan and/or where present of the intake duct. The camera may therefore be outside of a main airflow drawn into the fan when the fan is operating.

This positioning may reduce the aerodynamic disturbance created by the camera on air entering the fan. Additionally or alternatively the camera may be positioned so as to increase its detection of radiation emitted from the electromagnetic radiation emitter and backscattered on condensation within the detection region.

In some embodiments the electromagnetic radiation emitter emits monochromatic radiation. Alternatively the emitted radiation may be filtered to produce monochromatic radiation for passage through the detection region. Further the camera may be arranged to detect only the wavelength emitted (or filtered for), or otherwise only a narrow band of wavelengths encompassing the emitted/filtered for wavelength. Emission and detection of a single wavelength may reduce signal noise and therefore any filtering that is necessary.

In some embodiments the monochromatic radiation has a wavelength between 300 nm and 1100 nm or between 400 nm and 800 nm or between 450 nm and 600 nm or is substantially 500 nm. Some wavelengths may produce more scattering events with water droplets in condensation than others. Additionally some wavelengths may be better suited to image processing techniques.

In some embodiments the system comprises a fan test rig comprising the locating structure. The fan test rig may be adapted to mount a gas turbine engine fan thereon and/or to locate such a fan with respect to detection and/or instrumentation equipment.

In some embodiments the system comprises a gas turbine engine comprising the locating structure. The engine may for example be arranged for aero, marine or industrial power generation.

In some embodiments the electromagnetic radiation emitter is a laser. In alternative embodiments however the emitter may be a light emitting diode.

In some embodiments the system comprises a lens system arranged to convert the emitted radiation into a substantially planar sheet for passage across the detection region. A planar sheet may provide additional area coverage by comparison with discrete electromagnetic beams passing through the detection area.

In some embodiments the system comprises a data transmitter and an image processor, the data transmitter being arranged to transmit detected radiation data from the camera to the image processor. The image processor may use image processing software to search for the presence of condensation. Determination of the presence of condensation may be based on the quantity of radiation received by the camera. The processor may also use the image processing software to determine the location of any condensation within the detection region and optionally produce a condensation map of the detection region. The processing may be performed in real time. The detection of condensation may give rise to an alert such as an alarm. A condensation map may be useful in analysing why condensation has formed and predicting future condensation formation.

In some embodiments at least two of the electromagnetic radiation emitters are provided. At least two radiation emitters may be necessary in order that complete radiation coverage of the area adjacent and in front of the fan is achieved. In particular a nose cone of the fan may cast a radiation shadow with respect to radiation coming from any particular direction. Further where no lens system is provided and radiation beams are used in a net configuration, additional emitters may increase the area covered. As will be appreciated all previously discussed features and relationships of the electromagnetic radiation emitter may apply to any one, some or all of any additional electromagnetic radiation emitters provided.

In some embodiments at least two of the cameras are provided. Further it may be that all parts of the detection region are in the field of view of at least one of the cameras. Aside from ensuring that the whole of the detection region is covered by cameras (which may not be possible with a single camera positioned outside of a region where the main flow passes before entering the fan), at least two cameras may provide a stereoscopic view. This may allow condensation detection and/or mapping for a three dimensional detection region. As will be appreciated all previously discussed features and relationships of the camera may apply to any one, some or all of any additional cameras provided.

According to a second aspect there is provided a method of detecting condensation occurring within a detection region adjacent an upstream side of a gas turbine engine fan, the method comprising irradiating the detection region with electromagnetic radiation and detecting electromagnetic radiation backscattered on any condensation present.

The skilled person will appreciate that except where mutually exclusive, a feature described in relation to any one of the above aspects may be applied mutatis mutandis to any other aspect. Furthermore except where mutually exclusive any feature described herein may be applied to any aspect and/or combined with any other feature described herein.

Figure 2:
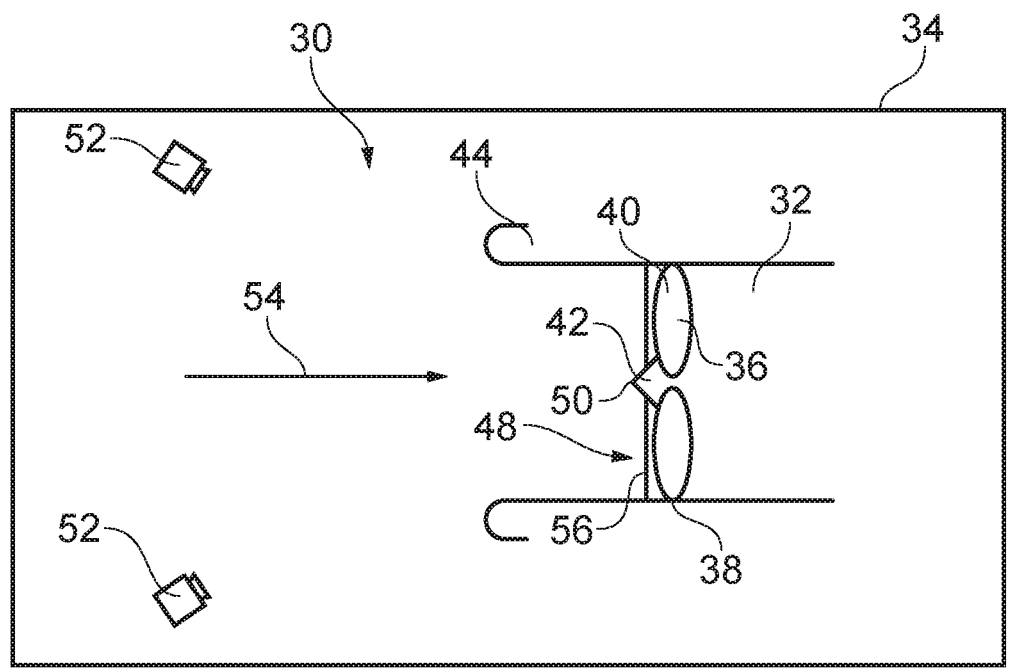
Figure 3:
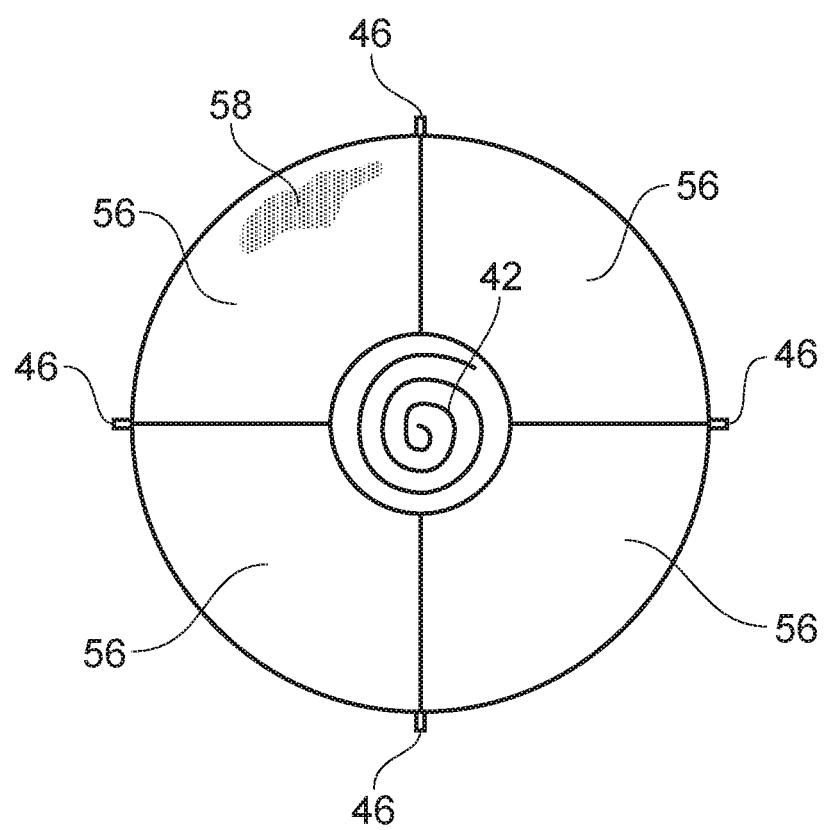

Embodiments will now be described by way of example only, with reference to the Figures, in which:

FIG. 1 is a sectional side view of a gas turbine engine;
FIG. 2 is a side view of an embodiment of the invention;
FIG. 3 is a front view of an embodiment of the invention.

With reference to FIG. 1, a gas turbine engine is generally indicated at 10, having a principal and rotational axis 11. The engine 10 comprises, in axial flow series, an air intake 12, a propulsive fan 13, an intermediate pressure compressor 14, a high-pressure compressor 15, combustion equipment 16, a high-pressure turbine 17, an intermediate pressure turbine 18, a low-pressure turbine 19 and an exhaust nozzle 20. A nacelle 21 generally surrounds the engine 10 and defines both the intake 12 and the exhaust nozzle 20.

The gas turbine engine 10 works in the conventional manner so that air entering the intake 12 is accelerated by the fan 13 to produce two air flows: a first air flow into the intermediate pressure compressor 14 and a second air flow which passes through a bypass duct 22 to provide propulsive thrust. The intermediate pressure compressor 14 compresses the air flow directed into it before delivering that air to the high pressure compressor 15 where further compression takes place.

The compressed air exhausted from the high-pressure compressor 15 is directed into the combustion equipment 16 where it is mixed with fuel and the mixture combusted. The resultant hot combustion products then expand through, and thereby drive the high, intermediate and low-pressure turbines 17, 18, 19 before being exhausted through the nozzle 20 to provide additional propulsive thrust. The high 17, intermediate 18 and low 19 pressure turbines drive respectively the high pressure compressor 15, intermediate pressure compressor 14 and fan 13, each by suitable interconnecting shaft.

Other gas turbine engines to which the present disclosure may be applied may have alternative configurations. By way of example such engines may have an alternative number of interconnecting shafts (e.g. two) and/or an alternative number of compressors and/or turbines. Further the engine may comprise a gearbox provided in the drive train from a turbine to a compressor and/or fan.

Referring now to FIGS. 2 and 3 a condensation irradiation system is generally shown at 30. The condensation irradiation system comprises a gas turbine engine 32 shown within a test cell 34. The gas turbine engine 32 is a turbofan engine and therefore has a fan 36. The fan 36 defines a fan plane that passes through the tip 38 of each fan blade 40. The fan 36 has a spinner 42 at its centre and is surrounded by an intake duct which is itself surrounded by a nacelle 44. The intake duct forms part of a locating structure which locates four electromagnetic radiation emitters 46 with respect to the fan 36. The electromagnetic radiation emitters 46 are evenly distributed circumferentially about the intake duct and positioned so as to all lie in an emitter plane, upstream of the fan 36 and parallel to the fan plane. Depending on the embodiment the emitters 46 may be intrinsically provided as part of the intake duct or may alternatively be retrofitted for operation within the test cell 34. Associated with each electromagnetic radiation emitter 46 is a lens of a lens system (not shown).

Adjacent and upstream of the fan 36 and bounded by the intake duct is a condensation detection region generally provided at 48. The detection region 48 is further bounded on an upstream side by a spinner tip plane parallel to the fan plane and passing through a tip 50 of the spinner 42 and on the downstream side by the fan plane. The condensation detection region 48 is therefore cylindrical in shape and the emitter plane divides the cylinder into two equal sized smaller cylinders.

The condensation irradiation system 30 further comprises a pair of cameras 52. The cameras 52 are positioned upstream of the fan 36 and detection region 48, beyond the upstream extent of the nacelle 44. The cameras 52 are also positioned outside of an axial projection of the fan 36 and of the intake duct. The cameras 52 are therefore out of a main airflow 54 drawn into the fan 36. The cameras 52 are positioned opposite each other and are directed with their fields of view towards the detection region 48. The whole of the detection region 48 is within the combined fields of view of the cameras 52. In this embodiment the cameras 52 are mounted to the walls of the test cell 34 and are therefore mounted separately to the locating structure. In other embodiments however (especially where the cameras 52 are provided embedded within the nacelle or where the fan is mounted via a fan test rig rather than by a whole engine) the cameras 52 may be mounted on the locating structure.

In use of the condensation irradiation system 30, the gas turbine engine 32 is placed into the test cell 34. The engine 32 is secured in a predetermined position and orientation with respect to the test cell 34 and the cameras 52 before it is started. Each electromagnetic radiation emitter 46 emits a constant beam of monochromatic laser light. Each beam is shaped by the lens associated with each emitter 46 into a substantially planar sheet 56 which passes across the detection region 48. The planar sheets 56 pass through the detection region 48 travelling in a direction substantially parallel to the fan plane. The planar sheets 56 form a near complete detection net across the intake duct.

The cameras 52 film the detection region 48 and are sensitive only to the wavelength of the laser light emitted by the emitters 46. The cameras 52 film consistently throughout the engine 32 run and transmit data pertaining to the captured images to an image processor (not shown) via a data transmitter. The processor utilises image processing software stored on a memory to analyse the images (e.g. filtering to remove noise and searching for evidence of condensation 58). If the image processing reveals that condensation is present an alarm to this effect is triggered by the processor and is shown on a user display. The data recorded by the cameras 52 is also stored in the memory for optional subsequent analysis. The filming, transmission, image processing, alarm display and data storage steps occur in real-time whilst the engine 32 is running.

In the event that condensation 58 occurs within the detection region 48, laser light of a sheet 56 may irradiate droplets within the condensation and may be scattered in the direction of one or other of the cameras 52. At least one of the cameras 52 may capture this light and trigger the issuing of the alarm.

As will be appreciated, in some embodiment the image processor may also map the condensation present in terms of its distribution at a particular time or over a period of time. The latter in particular may offer improved understanding of the development and evolution of the condensation. Additionally, in areas of the detection region filmed by at least two cameras, mapping may be performed in three dimensions, as facilitated by the stereoscopic view provided by the cameras. Maps may be displayed on the user display and/or recorded in the memory.

The triggering of the alarm and/or analysis of the maps may give rise to termination of the engine run and/or the application of condensation compensation factors applied to other test data (e.g. pressure ratio across the fan and fan inlet temperature). collected during the engine run Additionally or alternatively such data may be used to better understand the ambient and/or engine operating conditions which can be expected to give rise to condensation formation, and may be used to set conditions which must be met before future engine runs are undertaken.

It will be understood that the invention is not limited to the embodiments above-described and various modifications and improvements can be made without departing from the concepts described herein. By way of example it may be that the gas turbine engine and/or test cell are replaced with a fan test rig that may for instance comprise a frame as the locating structure on which may be mounted the emitters and optionally the cameras and/or fan. Such a rig may also be provided with an intake duct. By way of further example, other embodiments may be implemented in the context of an in service engine and not therefore in a specific test environment. In this case it may be that the camera(s) are integrated into the intake duct. Except where mutually exclusive, any of the features may be employed separately or in combination with any other features and the disclosure extends to and includes all combinations and sub-combinations of one or more features described herein.

The invention claimed is:

1. A condensation irradiation system comprising:
   a locating structure having a gas turbine engine fan;
   an electromagnetic radiation emitter mounted on the locating structure, the radiation emitter being configured to emit electromagnetic radiation through a condensation detection region adjacent to an upstream side of the gas turbine engine fan; and
   a sensor configured to detect a presence of condensation in the condensation detection region by scattering of the electromagnetic radiation within the condensation detection region.

2. The condensation irradiation system according to claim 1, wherein the detection region is a space bounded by planes that are substantially parallel with the fan plane.

3. The condensation irradiation system according to claim 1, wherein the emitted electromagnetic radiation passes through the detection region travelling in a direction substantially parallel to the fan plane.

4. The condensation irradiation system according to claim 1, wherein the system comprises the fan.

5. The condensation irradiation system according to claim 1, wherein the detection region is downstream of a radial plane passing through a tip of a nose cone of the fan.

6. The condensation irradiation system according to claim 1, wherein the sensor includes a camera oriented so as at least part of the detection region is within a field of view of the camera.

7. The condensation irradiation system according to claim 6, wherein the camera is positioned outside of an axial projection of the fan.

8. The condensation irradiation system according to claim 6, wherein the electromagnetic radiation emitter emits monochromatic radiation and the camera is arranged to detect only the wavelength emitted.

9. The condensation irradiation system according to claim 6, wherein at least two of the cameras are provided and an entirety of the detection region is in the field of view of at least one of the cameras.

10. The condensation irradiation system according to claim 1, further comprising a fan test rig having the locating structure.

11. The condensation irradiation system according to claim 1, further comprising a gas turbine engine having the locating structure.

12. The condensation irradiation system according to claim 1, wherein the electromagnetic radiation emitter is a laser.

13. The condensation irradiation system according to claim 1, further comprising a lens system configured to convert the emitted radiation into a substantially planar sheet for passage across the detection region.

14. The condensation irradiation system according to claim 1, wherein at least two of the electromagnetic radiation emitters are provided.

15. A method of detecting condensation occurring within a condensation detection region adjacent an upstream side of a gas turbine engine fan, the method comprising:
   providing a locating structure having the gas turbine engine fan;
   providing an electromagnetic radiation emitter mounted on the locating structure;
   irradiating, by the radiation emitter, the condensation detection region with electromagnetic radiation; and
   detecting, by a sensor, a presence of condensation in the condensation detection region by scattering of the electromagnetic radiation within the condensation detection region.

* * * * *